United States Patent
Jonsson et al.

(10) Patent No.: US 11,007,091 B2
(45) Date of Patent: May 18, 2021

(54) TAMPON APPLICATOR (71) Applicant: Essity Hygiene and Health Aktiebolag, Gothenburg (SE)

(72) Inventors: Sylvia Jonsson, Gothenburg (SE); Conny Dahlqvist, Gothenburg (SE); Susanne Carlstedt, Malmö (SE); Malkus Arlemark, Malmö (SE)

(73) Assignee: Essity Hygiene and Health Aktiebolag, Gothenburg (SE)

( * ) Notice: Subject to any disclaimer, the term of this patent is extended or adjusted under 35 U.S.C. 154(b) by 0 days.

(21) Appl. No.: 16/652,281

(22) PCT Filed: Oct. 6, 2017

(86) PCT No.: PCT/EP2017/075543
§ 371 (c)(1),
(2) Date: Mar. 30, 2020

(87) PCT Pub. No.: WO2019/068351
PCT Pub. Date: Apr. 11, 2019

(65) Prior Publication Data
US 2020/0237575 A1    Jul. 30, 2020

(51) Int. Cl.
*A61F 13/26* (2006.01)
(52) U.S. Cl.
CPC ................... *A61F 13/266* (2013.01)
(58) Field of Classification Search
CPC .... A61F 13/26; A61F 13/266; A61F 13/2022; A61F 13/2037; A61F 6/12; A61F 6/18
See application file for complete search history.

(56) References Cited

U.S. PATENT DOCUMENTS

| 3,765,416 A | 10/1973 | Werner et al. |
| 4,361,150 A | 11/1982 | Voss |

(Continued)

FOREIGN PATENT DOCUMENTS

| CN | 1229351 A | 9/1999 |
| CN | 101155568 A | 4/2008 |

(Continued)

OTHER PUBLICATIONS

International Preliminary Report on Patentability for International Application No. PCT/EP2017/075539, dated Sep. 16, 2019, 12 pages.

(Continued)

Primary Examiner — Tatyana Zalukaeva
Assistant Examiner — Heather K Barnwell
(74) Attorney, Agent, or Firm — Wood Herron & Evans LLP (57) ABSTRACT An applicator for a tampon comprising an inner tube slideable within an outer tube is provided. A plurality of protrusions is provided on the outer surface of the inner tube at its forward end and a plurality of spikes is provided on the inner surface of the outer tube at its forward end. The applicator has one or more of these features: i) the same or different number of protrusions and spikes; ii) one or more of the protrusions are arranged in an asymmetric manner around the outer surface of the inner tube such that the distance between two adjacent protrusions is not the same for all adjacent pairs of protrusions; iii) one or more of the spikes are arranged in an asymmetric manner around the inner surface of the outer tube such that the distance between two adjacent spikes is not the same for all adjacent pairs of spikes.

15 Claims, 5 Drawing Sheets

(56) References Cited

U.S. PATENT DOCUMENTS

| | | | |
|---|---|---|---|
| 4,479,791 A * | 10/1984 | Sprague | A61F 13/263 604/14 |
| 4,676,773 A | 6/1987 | Sheldon | |
| 4,960,417 A | 10/1990 | Tarr et al. | |
| 5,080,659 A | 1/1992 | Nakanishi | |
| 5,554,109 A | 9/1996 | Frayman | |
| 5,569,177 A * | 10/1996 | Fox | A61F 13/26 604/15 |
| 5,571,540 A | 11/1996 | Weyenberg et al. | |
| 2003/0028138 A1 | 2/2003 | Karapasha et al. | |
| 2003/0144639 A1 | 7/2003 | Gehling | |
| 2005/0273043 A1 | 12/2005 | Osborn et al. | |
| 2008/0154176 A1 * | 6/2008 | Van Ingelgem | A61F 13/26 604/18 |
| 2008/0195029 A1 * | 8/2008 | Van Ingelem | A61F 13/2034 604/14 |
| 2009/0192436 A1 | 7/2009 | Karapasha et al. | |
| 2010/0016780 A1 | 1/2010 | VanDenBogart et al. | |
| 2010/0324468 A1 | 12/2010 | Gann et al. | |
| 2011/0201992 A1 * | 8/2011 | Smet | A61F 13/266 604/11 |
| 2011/0273727 A1 | 11/2011 | Seki et al. | |
| 2016/0296380 A1 | 10/2016 | Graham et al. | |

FOREIGN PATENT DOCUMENTS

| | | |
|---|---|---|
| CN | 101346114 A | 1/2009 |
| CN | 102088942 A | 6/2011 |
| CN | 102341080 A | 2/2012 |
| CN | 103384508 A | 11/2013 |
| CN | 206007475 U | 3/2017 |
| EP | 1695680 A1 | 8/2006 |
| EP | 1704841 A1 | 9/2006 |
| EP | 2404585 A1 | 1/2012 |
| GB | 2220359 A | 1/1990 |
| RU | 2406473 C2 | 12/2010 |
| WO | 2007115091 A1 | 10/2007 |
| WO | 2010046478 A1 | 4/2010 |
| WO | 2016156403 A1 | 10/2016 |

OTHER PUBLICATIONS

International Search Report and Written Opinion for International Application PCTEP2017/075539, dated Jan. 25, 2018, 11 pages.
International Search Report and Written Opinion for International Application No. PCT/EP2017/075541, dated Feb. 12, 2018, 8 pages.
International Preliminary Report on Patentability for International Application No. PCT/EP2017/075542, dated Sep. 2019, 11 pages.
International Search Report and Written Opinion for International Application PCT/EP2017/075542, dated Feb. 14, 2018, 9 pages.
International Preliminary Report on Patentability for International Application No. PCT/EP2017/075543, dated Sep. 18, 2019, 13 pages.
International Search Report and Written Opinion for International Application PCT/EP2017/075543, dated Feb. 14, 2018, 8 pages.
Federal Service for Intellectual Property, Decision to Grant, Russian Application No. 2020115156, dated Aug. 27, 2020 (17 pages).
Federal Service for Intellectual Property, Decision to Grant, Russian Application No. 2020115119, dated Aug. 14, 2020 (18 pages).
Federal Service for Intellectual Property, Decision to Grant, Russian Application No. 2020115036, dated Aug. 14, 2020 (18 pages).
China National Intellectual Property Administration, Office Action, Application No. 201780094581.1, dated Aug. 10, 2020 (8 pages).
China National Intellectual Property Administration, Office Action, Application No. 201780094573.7, dated Aug. 7, 2020 (10 pages).
China National Intellectual Property Administration, Office Action, Application No. 201780094572.2, dated Aug. 7, 2020 (11 pages).

\* cited by examiner

SECTION A-A

TAMPON APPLICATOR

CROSS REFERENCE TO RELATED APPLICATIONS

This is a U.S. National Phase application of PCT/EP2017/075543, filed Oct. 6, 2017, the disclosure of which is incorporated herein by reference in its entirety for all purposes.

TECHNICAL FIELD

The present disclosure relates to tampon applicators.

BACKGROUND

Tampons are female hygiene absorbent products used to absorb menstrual blood flow within the body of a user. Tampons may be provided with or without applicators. When no applicator is provided, the tampon is generally inserted manually by the user. However many women prefer to use an applicator to facilitate insertion of the tampon and/or for hygiene reasons.

Known tampon applicators generally include two cylindrical tubes arranged in a telescopic relationship with each other, one tube being slideable within the other tube. In one arrangement, the tampon is provided within the outer tube whilst the inner tube is provided within the outer tube behind the tampon and extending outside of the outer tube in a rearward direction. In use, the user inserts the outer tube into the body and pushes the rearwardly extending portion of the inner tube in a forward direction towards the tampon, and the front part of the inner tube makes contact with and pushes the tampon out of the outer tube and into the body of the user. It will be appreciated that, as the inner tube is only partially inserted into the outer tube, such applicators are relatively bulky.

In another arrangement, where the applicators may be referred to as "compact" or "collapsible" applicators, the tampon is located in the inner tube and the inner tube is almost entirely contained within the outer tube. This provides a more compact and discreet applicator. In such applicators, in use, the user first pulls an exposed rear part of the inner tube in a rearward direction so that the inner tube slides rearwardly with respect to the outer tube, thereby exposing most of the inner tube. Whilst the inner tube is being slid relative to the outer tube, the front end of the tampon may be engaged by the outer tube to help to hold the tampon in place whilst the inner tube is being rearwardly extended. In this manner, the tampon stays in position with respect to the outer tube whilst the inner tube slides backwards and extends rearwardly of the outer tube. This movement of the inner tube relative to the tampon and the outer tube results in the inner tube sliding in a rearward direction over the tampon and leaving the tampon within the outer tube. Once the tampon is no longer held within the inner tube and the inner tube is positioned rearwardly of the tampon, the outer tube may be inserted into the body of the user and the rearwardly extending portion of the inner tube may be pushed in a forward direction towards the tampon. The front part of the inner tube ideally then makes contact with the tampon and pushes the tampon out of the outer tube and into the body of the user.

It would be desirable to provide an applicator that is of the compact type and which permits a user to more accurately, easily and comfortably insert a tampon into the body.

SUMMARY

According to the present disclosure there is provided an applicator for a tampon comprising an inner tube and an outer tube, the inner tube being slideable within the outer tube, the applicator having a forward end, wherein a plurality of protrusions is provided on the outer surface of the inner tube at its forward end and a plurality of spikes is provided on the inner surface of the outer tube at its forward end, and wherein the applicator comprises one or more of the following features:

the number of protrusions at the forward end of the inner tube is not the same as the number of spikes at the forward end of the outer tube;

the number of protrusions at the forward end of the inner tube is the same as the number of spikes at the forward end of the outer tube and one or more of the protrusions are arranged in an asymmetric manner around the outer surface of the inner tube such that the distance between two adjacent protrusions is not the same for all adjacent pairs of protrusions;

the number of protrusions at the forward end of the inner tube is the same as the number of spikes at the forward end of the outer tube and one or more of the spikes are arranged in an asymmetric manner around the inner surface of the outer tube such that the distance between two adjacent spikes is not the same for all adjacent pairs of spikes.

Where a different number of spikes and protrusions are provided, the spikes and protrusions may be arranged at different or irregular intervals around the circumference of their respective tubes. Preferably, in an embodiment, the distance between two adjacent protrusions is not the same as the distance between two adjacent spikes. This may further help to prevent the spikes and protrusions from undesirably engaging each other.

The applicator may be of a compact type. The inner tube of the applicator may be configured to receive a tampon. The forward end refers to the front or distal end of the applicator, ie the part of the applicator which is inserted into the body. The rear or rearward end refers to the back or proximal end of the applicator, ie the part of the applicator which is not inserted into the body and which is handled by the user.

The inner surface of the outer tube may comprise an annular protrusion near to the rear end of the outer tube. The protrusions provided on the outer surface of the inner tube may be sized such that the internal diameter of the outer tube at the location of the annular protrusion may be smaller than the external diameter of the inner tube including the protrusions provided thereon. This enables the protrusions on the outer surface of the inner tube to engage with the annular protrusion on the inner surface of the outer tube to thereby prevent the inner tube from sliding completely out of the outer tube at the rear end of the outer tube.

The spikes provided on the inner surface of the outer tube may engage with the forward end of the tampon to hold the tampon in position, relative to the outer tube, whilst the inner tube is slid rearwards relative to the outer tube. The tampon may then exit the inner tube via the front end of the inner tube and be positioned in the outer tube with the inner tube being positioned behind the tampon, ready to push the tampon forwards and out of the front end of the outer tube.

When a user inserts a tampon using an applicator, it is desirable that a minimum amount of force is required to eject the tampon from the outer tube. This is because the user does not want to cause herself discomfort or pain if the tampon is not properly aligned with the vaginal cavity and is suddenly and forcefully ejected. New users of tampons, in particular, may find it difficult to correctly align and insert a tampon and are likely to be more cautious and to push out the tampon from the outer tube quite slowly.

However, when the applicator is provided with both spikes on the inner surface of the outer tube and protrusions on the outer surface of the inner tube, the spikes may undesirably engage with the protrusions when the applicator is in a more compact state (i.e. when the inner tube is located mainly within the outer tube), thereby making it difficult for a user to disengage the spikes from the protrusions and to slide the inner tube relative to the outer tube. In particular, when the inner tube is being pushed forwards into the outer tube to expel the tampon, if the spikes become engaged with the protrusions the inner tube may be prevented from being pushed as far as possible into the outer tube, thereby hindering the release of the tampon. A user may then have to use substantial force to push the inner tube further into the outer tube by forcing the protrusions past the spikes, which may be uncomfortable as explained above.

By providing a different number of spikes on the outer tube than protrusions on the inner tube and/or providing the spikes and/or protrusions asymmetrically around the circumference of their respective tubes such that the distance between two adjacent protrusions is not the same as the distance between two adjacent spikes, there is less chance that the spikes and the protrusions will undesirably engage with each other, or, if engagement occurs, it is likely to be between one spike and protrusion pair only, and not several pairs, thereby reducing the force required to fully push the inner tube into the outer tube. This makes use of the applicator easier and more comfortable.

The number of spikes at the forward end of the outer tube may be greater than the number of protrusions at the forward end of the inner tube. Alternatively the number of spikes at the forward end of the outer tube may be fewer than the number of protrusions at the forward end of the inner tube.

The inner tube may comprise a plurality of petals at its forward end. At least one protrusion of said plurality of protrusions may be provided on each petal of the inner tube. A single protrusion only may be provided on each petal of the inner tube. Alternatively, two or more protrusions may be provided on each petal of the inner tube.

One or more protrusions may be provided at the base of each petal on the outer surface of the inner tube.

Each protrusion may extend in a radially outward direction from the outer surface of the inner tube.

Each protrusion may extend from the base of a petal in the longitudinal direction of the inner tube towards the forward end of said petal.

The length of the protrusion in the direction of the longitudinal length of the inner tube may be at least a quarter of the distance between the base of the petal and the forward end of said petal.

The length of the protrusion in the direction of the longitudinal length of the inner tube may be greater than the width of the protrusion in a direction extending around the circumference of the inner tube. By providing protrusions of a relatively narrow width, there is less chance that the protrusion will undesirably engage with a spike.

The protrusion may be tapered along its longitudinal length, such that the height of the protrusion (the dimension of the protrusion in the radial direction of the inner tube) decreases towards the front end of the protrusion. By providing protrusions tapered in this manner, there is less chance that the protrusion will undesirably engage with a spike.

The protrusion may have a substantially constant width (its dimension in the direction extending around the circumference of the inner tube). Alternatively, the protrusion may have a width which tapers from the base of the petal (where the protrusion is at its widest) towards the forward end of the petal. The protrusion may have a substantially triangular shape in plan view (i.e. when viewed from directly above). The protrusion may have the shape of an isosceles triangle when viewed from above. The longitudinal length of the protrusion may be greater than the width of the protrusion at the base of the petal.

An even number of petals may be provided on the inner tube. The petals may be evenly spaced around the circumference of the inner tube. An even number of petals may be provided. Four petals may be provided.

The outer tube may comprise a plurality of petals at its forward end. At least one spike of said plurality of spikes may be provided on each petal of the outer tube. A single spike may be provided on each petal of the outer tube. Alternatively, two or more spikes may be provided on each petal of the outer tube.

One or more spikes may be provided at the base of each petal on the inner surface of the outer tube.

Each spike may extend from or near the base of a petal towards the forward end of said petal, this being the length of the spike.

The length of the spike may be greater than the width of the spike, the width being in a direction extending around the circumference of the outer tube. By providing spikes of a relatively narrow width, there is less chance that the spike will undesirably engage with a protrusion.

An odd number of petals may be provided on the outer tube. The petals may be evenly spaced around the circumference of the outer tube. Five petals may be provided on the outer tube.

The inner tube and the outer tube may be formed from a thermoplastic material, such as a medical device classified thermoplastic material for example. The inner and outer tube may be formed from low density polyethylene (LDPE). The inner tube may be formed from a more rigid material or a stiffer material than the outer tube. For example, the outer tube may be formed from LDPE and the inner tube may be formed from polypropylene (PP).

This permits the outer tube to be formed from a softer and/or more resilient material than the inner tube so that the outer tube is more comfortable when inserted into the body of a user. The inner tube may be formed of a more rigid material to assist in pushing the tampon out from the outer tube of the applicator into the body of a user. Where the inner tube is formed from a more rigid material than the outer tube, it may be desirable to provide more spikes on the outer tube than protrusions on the inner tube, as the spikes made from the less rigid material will give way under pressure more easily than the more rigid protrusions.

The applicator may further comprise a tampon disposed in the inner tube. The spikes may be configured to engage with the tampon.

BRIEF DESCRIPTION OF DRAWINGS

The present invention will now be described by way of example only and with reference to the following drawings, of which.

DETAILED DESCRIPTION OF PARTICULAR EMBODIMENTS

Figure 1:
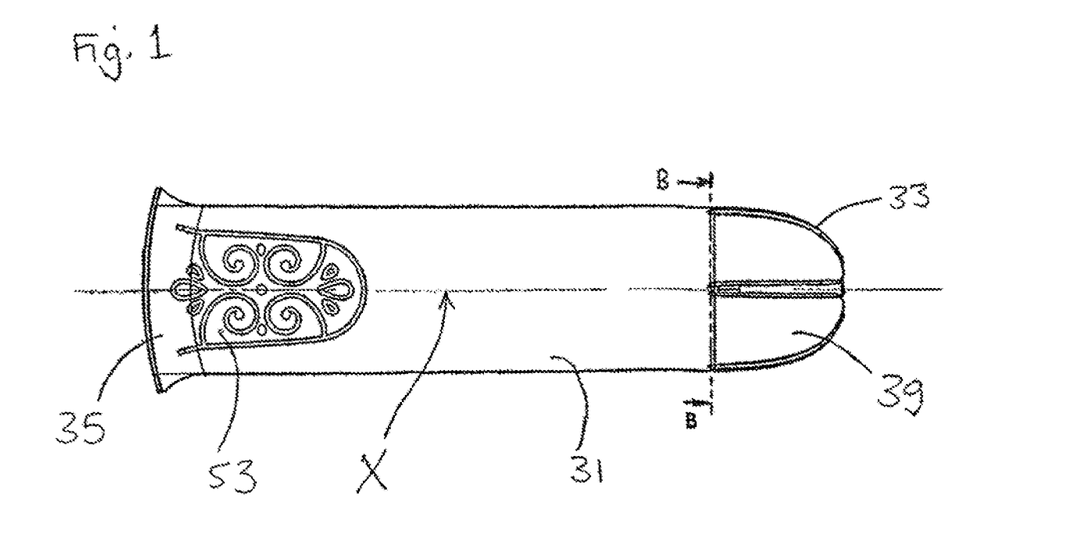
FIG. 1 shows a plan view of an outer tube of a tampon applicator in accordance with an embodiment of the invention.
Figure 2:
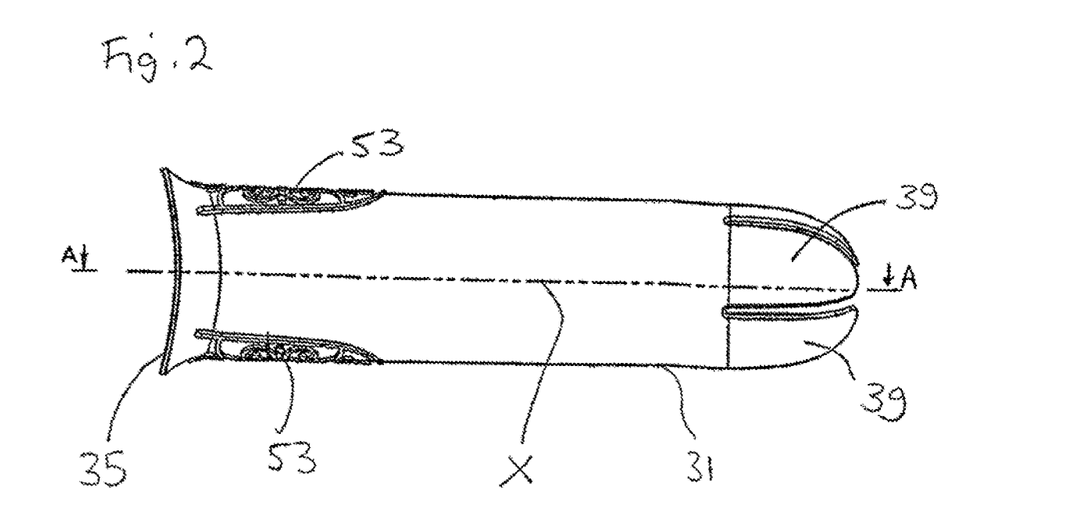
FIG. 2 shows a side view of the outer tube of FIG. 1.

An outer tube 31 of a tampon applicator is shown in FIGS. 1 and 2. The direction along the longitudinal axis of the outer tube is shown as X. The outer tube 31 has a front end 33 and a rear end 35. The front end 33 of the outer tube 31 includes a plurality of petals 39. In this depicted embodiment, five identical petals are provided, the petals being evenly spaced around the circumference of the outer tube. In other embodiments, the petals may not be identical, and/or may not be spaced evenly around the circumference of the inner tube. Fewer or more than five petals may be provided.

The external diameter of the outer tube 31 of FIG. 1 is tapered at its rearward end such that the external diameter of the outer tube increases towards the rear end 35 of the outer tube 31. In other embodiments, the external diameter of the outer tube may be not tapered.

In this depicted embodiment, a grip feature 53 is provided on the outer surface of the outer tube at its rear end. The grip feature may include, for example, a raised pattern or a different texture. In this depicted embodiment, there are two discrete grip features 53 provided which are positioned substantially diametrically opposite to each other on the outer surface of the outer tube. In other embodiments, a grip feature may extend around the external circumference of the outer tube.

In this embodiment, the longitudinal length of the outer tube 31 varies around the circumference due to the rear end 35 of the outer tube having a circumferential edge which is of a wave or undulating form. In this embodiment, the outer tube has a greater longitudinal length where the discrete grip features 53 are present and a smaller longitudinal length where the discrete grip features 53 are not present. In other embodiments, the outer tube 31 may be of a more regular form, having a longitudinal length which does not vary around the circumference.

Figure 3:
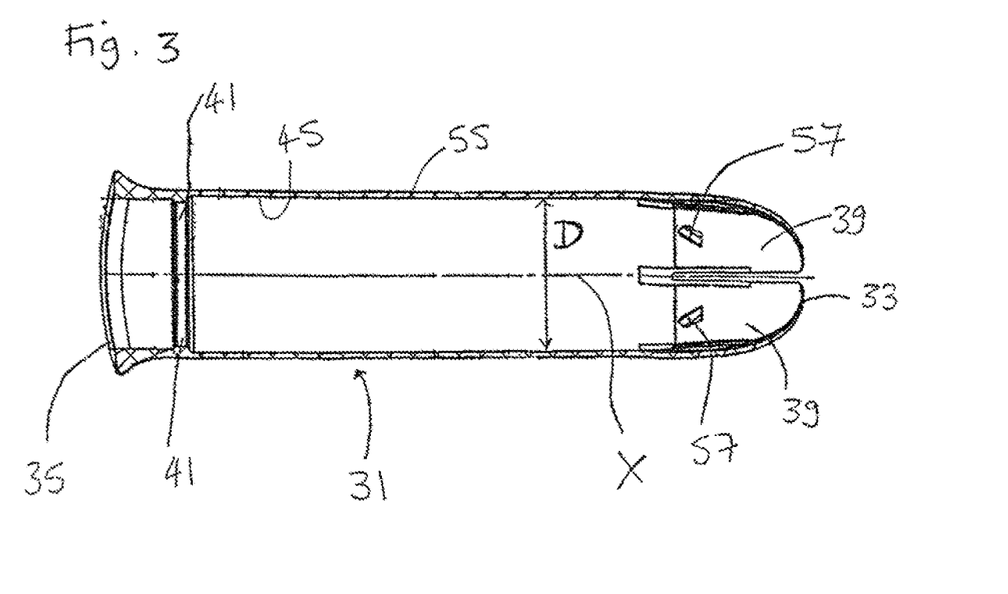
FIG. 3 shows the section A-A of the outer tube.

FIG. 3 shows the section A-A of the outer tube 31. An annular ring, rim or protrusion 41 may be provided within the outer tube 31 at or near to the rear end 35 of the outer tube 31 as shown in FIG. 3. The annular protrusion 41 of the outer tube may extend radially inwardly substantially at a right angle from the interior surface 45 of the outer tube 31. The annular protrusion may be used, in conjunction with protrusions provided on the outer surface of the inner tube, to retain the inner tube in the outer tube by stopping the inner tube from sliding completely out of the outer tube when the inner tube is slid backwards relative to the outer tube.

From FIG. 3 it can be seen that the main or central portion 55 of the outer tube 31 has an internal diameter D. The external diameter of the inner tube is smaller than D to permit the inner tube to slide within the outer tube 31.

FIG. 3 also shows a spike 57 provided on the inner surface of each of the petals 39 of the outer tube 31. In some embodiments, the spike may extend from the inner surface of the petal 39 towards the forward end of the petal. The spike 57 is configured to engage with the forward end of the tampon to hold the tampon in position, relative to the outer tube 31, whilst the inner tube is slid rearwards relative to the outer tube.

In the depicted embodiment, a spike 57 is provided at the base of each petal 39 on the inside surface of the outer tube. In other embodiments, a spike may be provided on the inside surface of the outer tube rearward of the petals, or alternatively a spike may be provided in the middle of a petal or towards the front end of a petal. In the depicted embodiment, one spike 57 is provided on each petal. In other embodiments, more than one spike may be provided on a petal.

Figure 4:
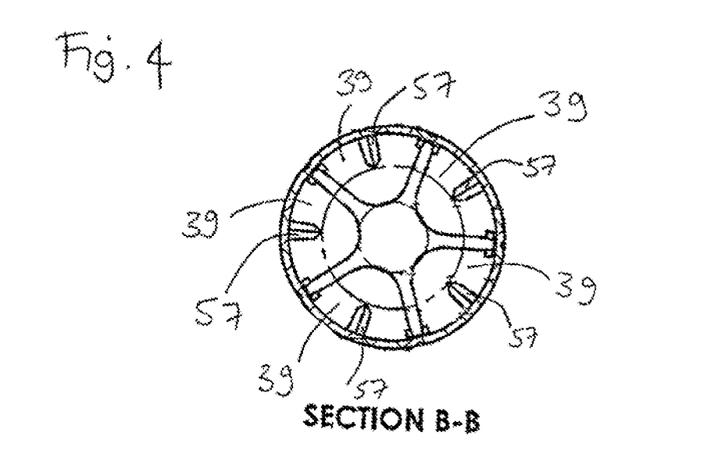
FIG. 4 shows the section B-B of the outer tube.

FIG. 4 shows the section B-B of the outer tube. The petals 39 and the spikes 57 can also be seen in this figure.

Figure 5:
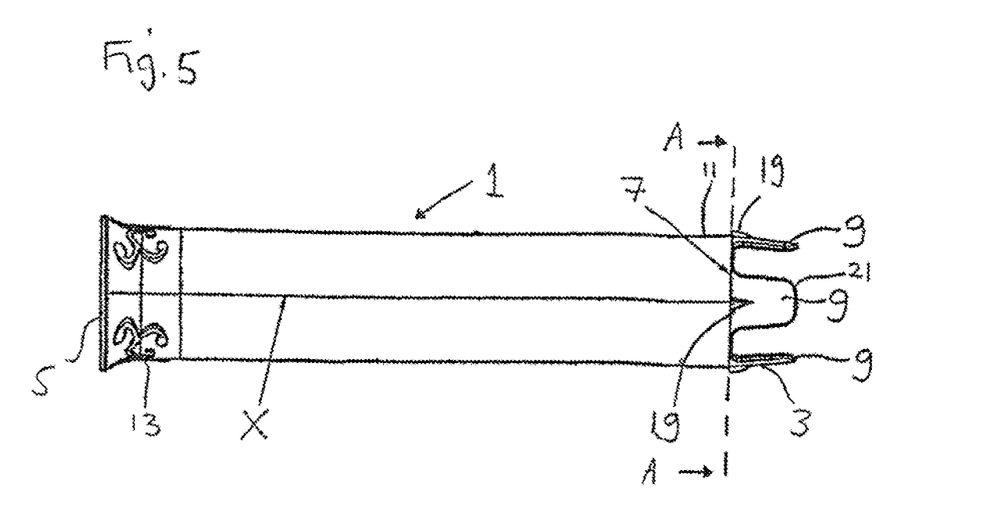
FIG. 5 shows a plan view of an inner tube in accordance with an embodiment of the invention.
Figure 6:
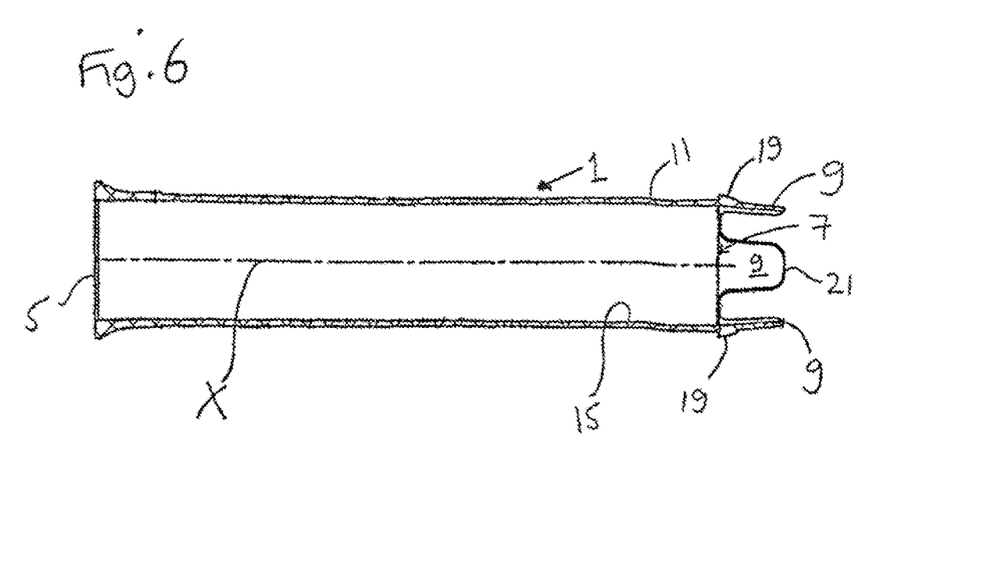
FIG. 6 shows a section through the inner tube of FIG. 5 along its longitudinal length.

FIGS. 5 and 6 show an inner tube 1 of a tampon applicator having a longitudinal axis X. The inner tube 1 has a front end 3 and a rear end 5. The front end 3 of the inner tube 1 includes a plurality of petals 9. In this depicted embodiment, four identical petals are provided, the petals being evenly spaced around the circumference of the inner tube. In other embodiments, the petals may not be identical, and/or may not be spaced evenly around the circumference of the inner tube. It is advantageous to provide at least two petals. In embodiments of the invention two, three, four, five, six or more petals may be provided.

A protrusion 19 may be provided at the base 7 of each petal 9. In this depicted embodiment, a single protrusion 19 is provided at the base 7 of each petal 9. However, in other embodiments two or more protrusions may be provided at the base of each petal. In other embodiments, one or more protrusions may be provided on a petal towards the middle of the petal rather than at the base of the petal. In further embodiments, one or more protrusions may instead be provided rearward of the petals 9 on the outer surface 11 of the inner tube 1.

In this depicted embodiment, the protrusions extend in a radially outward direction from the outer surface 11 of the inner tube 1. In this depicted embodiment, each protrusion 19 extends from the base 7 of a petal 9 in the longitudinal direction X of the inner tube towards the forward end 21 of the petal 9. The length of the protrusion 19 in the longitudinal direction X may be at least a quarter of the distance between the base 7 of the petal 9 and the forward end 21 of the petal 9, and may be a third or even a half of this distance.

Figure 7:
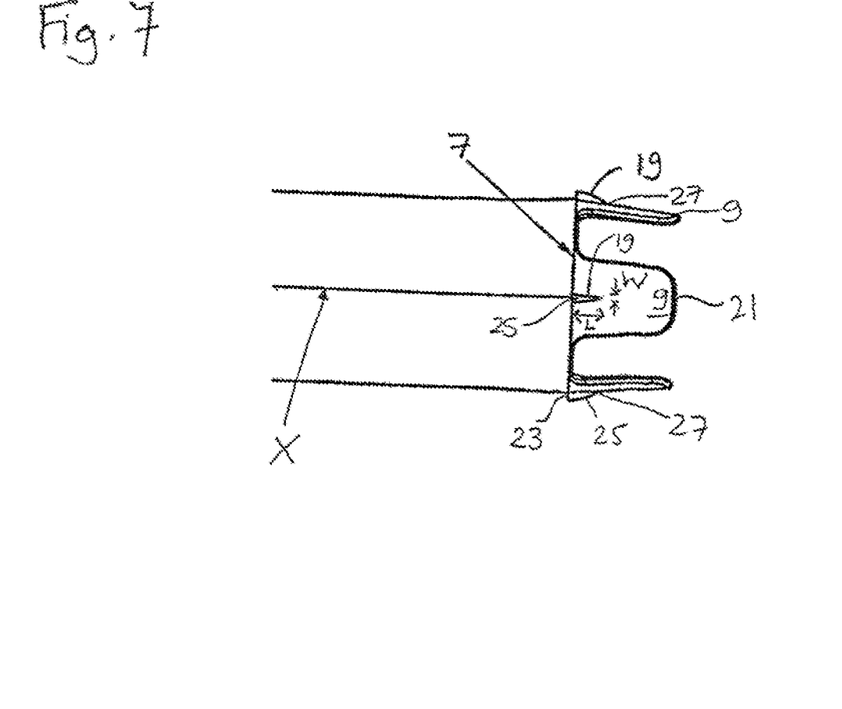
FIG. 7 shows an enlarged view of part of the inner tube of FIG. 6.

In this depicted embodiment, the protrusions 19 have a width W in a direction extending around the circumference of the inner tube 1 (as shown in FIG. 7). The protrusions 19 may have a width which tapers from the base 7 of the petal 9 (where the protrusion 19 is at its widest) towards the forward end 21 of the petal 9 giving the protrusions 19 a triangular shape as shown in FIGS. 5 and 7.

Alternatively, the protrusions 19 may have a substantially constant width W giving the protrusions 19 a rectangular shape when viewed from directly above.

The protrusions 19 may cause the petals 9 to bend inwards so that the forward end 3 of the inner tube has a tapered shape in the region of the petals 9, as can be seen in FIGS. 5 and 6. A tapered inner tube front end 3 may be beneficial for engaging with the rear end of a tampon and in pushing the tampon out of an outer tube of an applicator.

The rear end 5 of the inner tube 1 may be tapered such that the rear end 5 of the inner tube 1 is wider than the remainder of the inner tube 1. This may assist in preventing the inner tube from being pushed entirely within an outer tube. The rear end 5 of the inner tube may include decorative or grip features 13 which may assist a user to firmly grip the rear end 5 of the inner tube 1 between their fingers, thereby facilitating use of the applicator.

FIG. 7 shows an enlarged view of the forward part of the inner tube of FIG. 6. From FIG. 7 it can be seen that, in this depicted embodiment, the length L of the protrusions 19 in the longitudinal direction X is greater than the maximum width W of the protrusions in a direction extending around the circumference of the inner tube. In other embodiments, the length L may be equal to the width W or less than the width W. However, it is advantageous to provide protrusions 19 on the inner tube where the length L of the protrusions is greater than their width W. This is because protrusions having a smaller width W are less likely to become undesirably engaged with the spikes of the outer tube than protrusions having a larger width W. Providing protrusions having a tapered width may further help in preventing the spikes from engaging with the protrusions.

The protrusions 19 in the depicted embodiment have a substantially triangular shape. In other embodiments, the protrusions 19 may have another shape, such as rectangular or square shaped, for example.

In the depicted embodiment, the rear end surface 23 of the protrusion 19 extends in a substantially radial direction outwardly from the outer surface 11 of the inner tube 1, such that the angle between the rear end surface 23 of the protrusion 19 and the outer surface 11 of the inner tube 1 is approximately 90 degrees. This is advantageous where the outer tube is provided with an interior annular ring, rim or protrusion 41 as explained with reference to FIG. 3.

The hypotenuse surface 25 of the depicted triangular protrusion extends from the radially most distant part of the rear end surface 23 of the protrusion 19 to the forward end 27 of the protrusion 19, the forward end 27 of the protrusion 19 meeting the outer surface of the petal 9. In this embodiment, the hypotenuse surface 25 has a curved shape as can be seen in FIG. 7. This may assist the inner tube to slide in a forwards direction relative to the outer tube during insertion of a tampon into the body of a user, and may also assist the protrusions of the inner tube to slide in a forward direction past the spikes of the outer tube. In other embodiments, the hypotenuse surface 25 of the protrusion 19 may be a flat sloping surface rather than a curved one.

The petals 9 depicted in FIG. 7 are substantially "U"-shaped. However, the petals 9 may instead be of a rectangular or square shape, or may have a more rounded shape than that depicted in FIG. 7. It may be advantageous to provide a relatively blunt or only gently rounded forward end 21 of the petal 9, such as that shown in FIG. 7, so that the forward end 21 of the petal 9 presents a reasonably large pushing surface for pushing a tampon out of the outer tube and into the body of a user. In this manner the applied force can be distributed over a greater area and there is less risk of the forward end 21 of the petal 9 breaking or becoming entangled with or embedded in the tampon.

Figure 8:
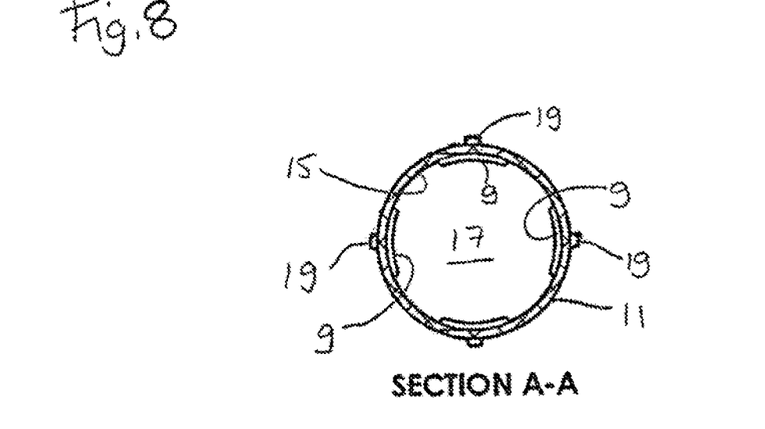
FIG. 8 shows the section A-A of the inner tube.

FIG. 8 shows a cross-section through the inner tube at the position shown as A-A in FIG. 5. The inner tube 1 defines an interior space 17 for receiving a tampon. The inner tube 1 has an inner surface 15 and an outer surface 11. The protrusions 19 and petals 9 can be seen in FIG. 8.

Figure 9:
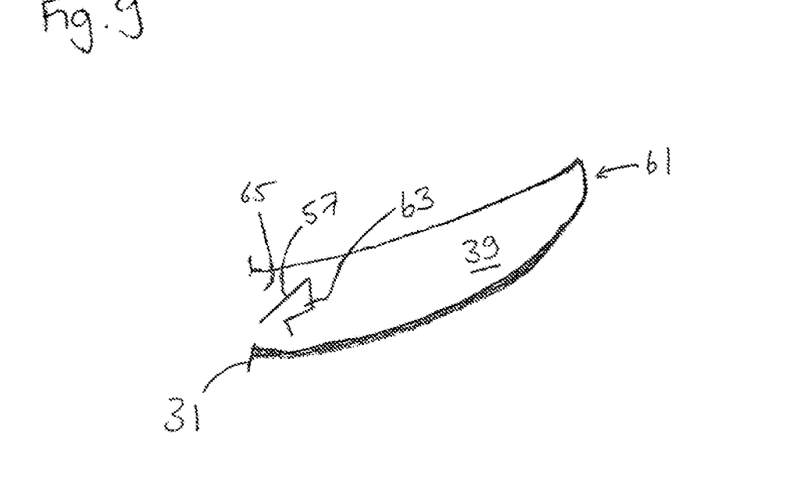
FIG. 9 shows an isometric view of a spike on the inside surface of a petal of the outer tube.

FIG. 9 shows an isometric view of a petal 39 of the outer tube 31 having a spike 57 located near the base 65 of the petal 39. In this depicted embodiment, the spike 57 is formed integrally with the petal and extends from the base 65 of the petal 39 towards the forward end 61 of the petal 39. In this depicted embodiment, it can be seen that the longitudinal length of the spike is greater than the width of the spike. In other embodiments, the longitudinal length of the spike may be the same as or less than the width of the spike. However, providing a spike having a greater length than width may advantageously help to prevent the spike from undesirably engaging with the protrusions 19 on the inner tube.

The spike 57 may have a barb 63 as shown in FIG. 9. The barb 63 may engage with the front part of the tampon to hold the tampon in position with regard to the outer tube whilst the inner tube is being slid in a rearward direction relative to the outer tube. This allows the inner tube to slide rearwards away from the tampon and to leave the tampon in the outer tube 31. The inner tube 1 is then positioned behind the tampon 51. The barb 57 may be configured to prevent or hinder rearward movement of the tampon relative to the outer tube but may permit the tampon to easily move forwards relative to the outer tube to allow the tampon to be expelled from the outer tube without the use of undue force.

Figure 10:
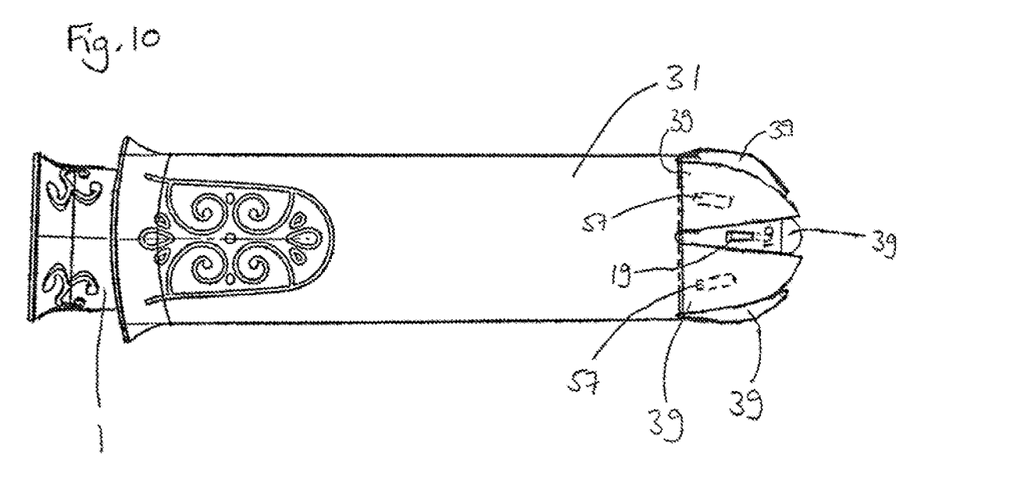
FIG. 10 shows a longitudinal side view of a tampon applicator in a compact state following ejection of the tampon in accordance with an embodiment of the invention.

FIG. 10 shows a tampon applicator in accordance with an embodiment of the invention. The applicator includes an inner tube 1 and an outer tube 31. FIG. 10 depicts the applicator following expulsion of the tampon from the applicator, with the inner tube 1 being pushed as far forward as possible within the outer tube 31. The petals 9 of the inner tube are now located almost as far forward as the petals 39 of the outer tube, and the petals 39 of the outer tube have been opened in a radially outward direction by the forward movement of the tampon and the inner tube. In FIG. 10, the petals 9 of the inner tube 1 can be seen between the petals 39 of the outer tube 31. A protrusion 19 can be seen on a petal 9 of the inner tube 1, the protrusion being located between two petals 39 of the outer tube. The petals 39 include spikes 57 which are located on the inner surface of the petals, and which are shown in dotted outline in FIG. 10. It can be seen that the spikes 57 are now located rearwardly of the protrusions 9. To enable the spikes and protrusions to slide past each other without engaging each other, it is desirable to provide spikes and protrusions of relatively narrow width. Furthermore, by providing a different number of protrusions than spikes, the protrusions and spikes may be arranged around the circumference of their respective tubes at different intervals, such that, even if one spike and protrusion pair engage, the others will not.

In this embodiment, four petals are provided on the inner tube and five on the outer tube, with each petal on the inner tube having one protrusion and each petal on the outer tube having one spike. In other embodiments, more or fewer petals may be provided on the inner tube and the outer tube. For example, an odd number of petals may be provided on one tube and an even number on the other tube. More petals and/or protrusions may be provided on the outer tube than on the inner tube. This may be advantageous particularly where the inner tube is formed from a more rigid material than the outer tube, as the material of the outer tube will be more flexible and will give way more readily, even if there are more spikes on it than protrusions on the inner tube.

As an alternative to providing a different number of protrusions and spikes, the same amount of spikes and protrusions may be provided and the spikes and/or protrusions may be arranged asymmetrically around the circumference of their respective tubes such that the distance between two adjacent protrusions is not the same as the distance between two adjacent spikes. This reduces the risk that the spikes and the protrusions will undesirably engage with each other during use of the applicator.

While the foregoing description and drawings represent exemplary embodiments of the present invention, it will be understood that various additions, modifications and substitutions may be made therein without departing from the spirit and scope of the present invention. In particular, it will be clear to those skilled in the art that the present invention may be embodied in other specific forms, structures, arrangements, proportions, and with other elements, materials, and components, without departing from the spirit or essential characteristics thereof. One skilled in the art will appreciate that the invention may be used with many modifications of structure, arrangement, proportions, materials, and components and otherwise, used in the practice of the invention, which are particularly adapted to specific environments and operative requirements without departing from the principles of the present invention. The presently disclosed embodiments are therefore to be considered in all respects as illustrative and not restrictive, the scope of the invention being indicated by the appended claims, and not limited to the foregoing description.

The invention claimed is:

1. An applicator for a tampon comprising an inner tube and an outer tube, the inner tube being slideable within the outer tube, the applicator having a forward end, wherein a plurality of protrusions is provided on an outer surface of the inner tube at its forward end and a plurality of spikes is provided on an inner surface of the outer tube at its forward end, and wherein the inner tube comprises a plurality of petals at its forward end, and wherein at least one of the plurality of protrusions extends from a base of at least one of the plurality of petals in a longitudinal direction of the inner tube towards a forward end of said at least one petal, and wherein the at least one protrusion has a width in a direction extending around a circumference of the inner tube and wherein the width of the at least one protrusion tapers from the base of the at least one petal, where the at least one protrusion is at its widest, towards the forward end of the at least one petal, and wherein the applicator further comprises one or more of the following features:
 a number of protrusions at the forward end of the inner tube is not the same as a number of spikes at the forward end of the outer tube;
 a number of protrusions at the forward end of the inner tube is the same as a number of spikes at the forward end of the outer tube and one or more of the protrusions are arranged in an asymmetric manner around the outer surface of the inner tube such that a distance between two adjacent protrusions is not the same for all adjacent pairs of protrusions;
 a number of protrusions at the forward end of the inner tube is the same as a number of spikes at the forward end of the outer tube and one or more of the spikes are arranged in an asymmetric manner around the inner surface of the outer tube such that a distance between two adjacent spikes is not the same for all adjacent pairs of spikes.

2. The applicator for a tampon in accordance with claim 1 wherein the outer tube comprises a plurality of petals at its forward end and at least one spike of said plurality of spikes is provided on each petal of the outer tube.

3. The applicator for a tampon in accordance with claim 2 wherein each spike has a length that extends from the base of a petal in the longitudinal direction of the outer tube towards the forward end of said petal.

4. The applicator for a tampon in accordance with claim 3 wherein the length of the spike is greater than a width of the spike, the width being in a direction extending around the circumference of the outer tube.

5. The applicator for a tampon in accordance with claim 2 wherein at least one spike of said plurality of spikes is provided at the base of each petal on the inner surface of the outer tube.

6. The applicator for a tampon in accordance with claim 2 wherein an odd number of petals are provided on the outer tube, the petals being evenly spaced around the circumference of the outer tube.

7. The applicator for a tampon according to claim 1 wherein the number of spikes at the forward end of the outer tube is greater than the number of protrusions at the forward end of the inner tube.

8. The applicator for a tampon according to claim 1 wherein the number of protrusions at the forward end of the inner tube is greater than the number of spikes at the forward end of the outer tube.

9. The applicator for a tampon according to claim 1 wherein at least one protrusion of said plurality of protrusions is provided on each petal of the inner tube.

10. The applicator for a tampon according to claim 1 wherein only one protrusion of said plurality of protrusions is provided on each petal of the inner tube.

11. The applicator for a tampon according to claim 1 wherein each protrusion extends in a radially outward direction from the outer surface of the inner tube.

12. The applicator for a tampon in accordance with claim 1 wherein a length of the at least one protrusion in the direction of a longitudinal length of the inner tube is at least a quarter of a distance between the base of the at least one petal and the forward end of said at least one petal.

13. The applicator for a tampon in accordance with claim 1 wherein a length of the at least one protrusion in the direction of a longitudinal length of the inner tube is greater than a width of the at least one protrusion in a direction extending around the circumference of the inner tube.

14. The applicator for a tampon in accordance with claim 1 wherein an even number of petals are provided on the inner tube, the petals being evenly spaced around the circumference of the inner tube.

15. The applicator for a tampon in accordance with claim 1 wherein the applicator further comprises a tampon disposed in the inner tube, the spikes being configured to engage with the tampon.

* * * * *